United States Patent [19]

Grant

[11] 4,415,011

[45] Nov. 15, 1983

[54] SAMPLE COLLECTOR

[75] Inventor: Douglas M. Grant, Lincoln, Nebr.

[73] Assignee: ISCO, Inc., Lincoln, Nebr.

[21] Appl. No.: 316,979

[22] Filed: Nov. 2, 1981

[51] Int. Cl.³ .......................... B65B 3/04; B67C 3/28
[52] U.S. Cl. ...................................... 141/284; 222/14; 73/3
[58] Field of Search ........................ 141/284, 250–283, 141/83; 222/14, 16, 22; 250/573–577; 356/435, 436; 235/92 FL; 73/3, 168

[56] References Cited

U.S. PATENT DOCUMENTS 4,331,262  5/1982  Snyder et al. ........................ 222/14

Primary Examiner—Houston S. Bell, Jr.

Attorney, Agent, or Firm—Vincent L. Carney

[57] ABSTRACT

To collect a series of liquid samples each of which has a fixed volume in a corresponding series of sample bottles, a sample collector includes a control circuit that initiates the sampling at preset time intervals or each time a preset volume of liquid has flowed past the collector as indicated by a flow meter. To control the volume of each sample, an optical liquid interface detector within the flow passage of the sample collector initiates counting of the revolutions of the pump and after a pre-selected number of counts, the control circuit terminates the pumping. The optical liquid interface detector includes a light-emitting diode on one side of the flow passage and a phototransistor on the opposite side to detect the interface of the liquid.

10 Claims, 6 Drawing Figures

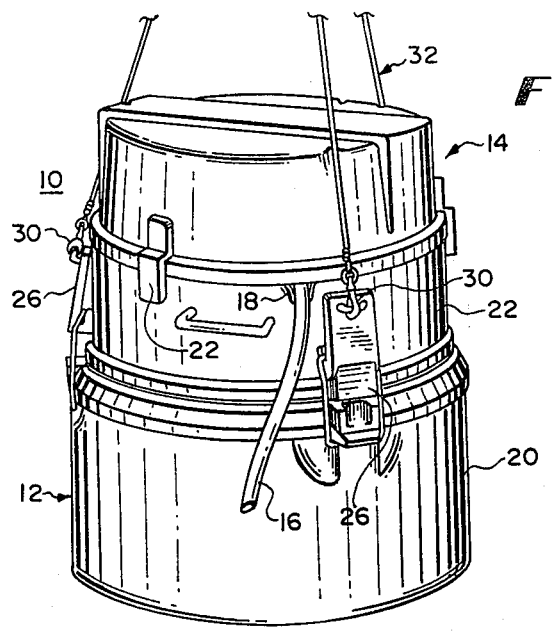
FIG. 1
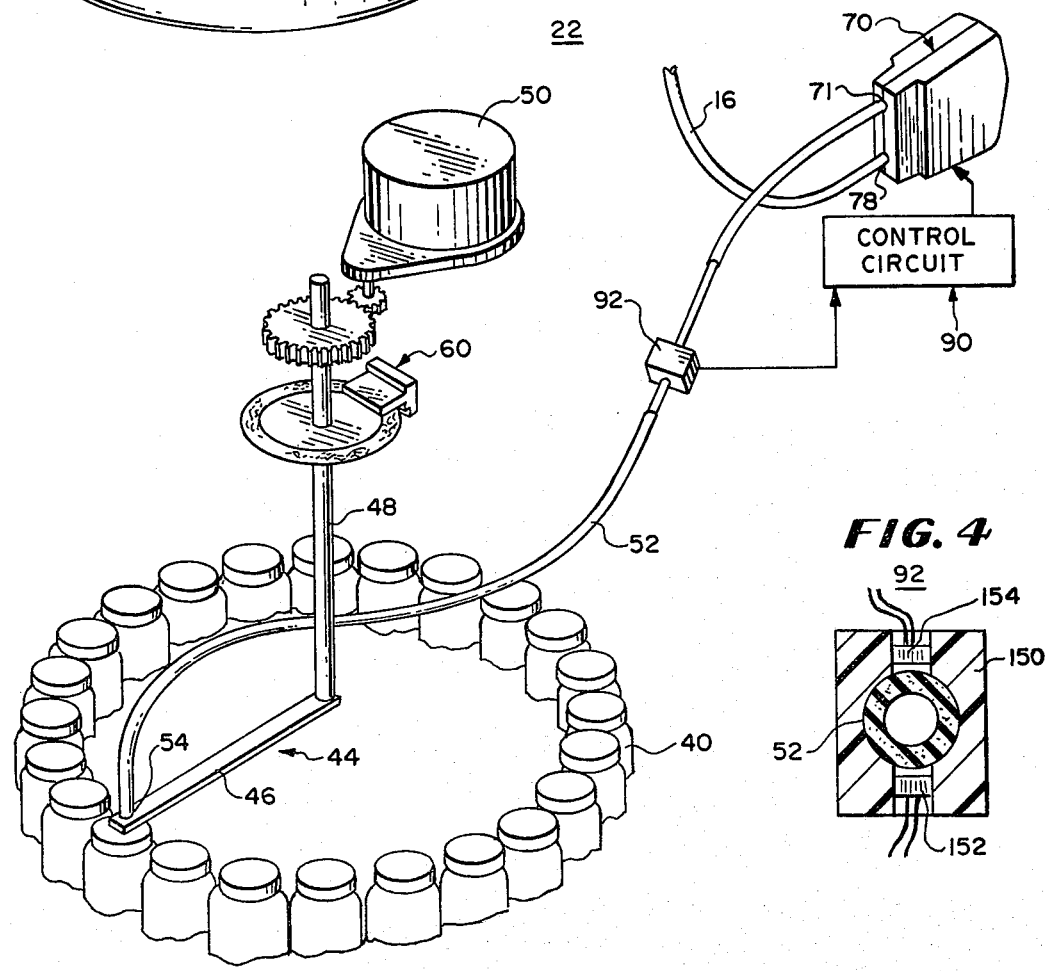
FIG. 3
FIG. 4

SAMPLE COLLECTOR

BACKGROUND OF THE INVENTION

This invention relates to sample collectors.

In one class of sample collector, a series of discrete volumes of liquid are collected within separate containers from a larger body of liquid for later analysis. They are collected by a pumping system that pumps samples from the liquid being monitored and deposits each of the samples into a different container.

In the prior art sample collectors of this class, the volume of each sample is controlled by depositing the sample in a separate measuring container and then emptying the container after the container is filled to a fixed volume or else controlling the amount of time or the number of strokes of the pump from the start of pumping until the liquid has been deposited into a sample collector or a combination of these two techniques.

The prior art systems have several disadvantages such as: (1) when a separate container is used, the opportunities for contamination are increased and the apparatus tends to be more complicated and expensive; and (2) when time or number of strokes are counted from the beginning of the sampling period, the volume varies under some circumstances with the viscosity of the fluid being pumped, with the escape of air and with similar variables.

SUMMARY OF THE INVENTION

It is an object of the invention to provide a novel sample collector.

It is a further object of the invention to provide a sample collector which accurately measures the volume of solids.

It is a still further object of the invention to provide a relatively simple sample collector.

It is a still further object of the invention to provide a sample collector in which the volume of the sample is measured starting at a time after the sample has reached a predetermined position in the sample line.

In accordance with the above and further objects of the invention, the sample collector includes a continuous flexible conduit mounted to cooperate with a peristaltic pump to pump samples from a body of liquid into containers. Apparatus is provided for moving one end of the conduit from container to container at preselected intervals of time.

To measure a preprogrammed amount of liquid into a container, an optical sensor is positioned adjacent to the continuous conduit to detect the interface of the liquid and to provide a signal. The number of strokes of the peristaltic pump are counted and controlled from the time of detection of the signal in accordance with the programmed volume, after which the direction of pumping is reversed to clear the conduit.

The optical sensor advantageously includes a source of light and a light sensor on opposite sides of the continuous conduit, where the liquid interface interrupts the light from the source to generate a signal indicating the interface. The light source may be a light-emitting diode and the sensor may be a phototransistor.

This sample collector has the advantages of: (1) utilizing a single continuous conduit which reduces contamination possibilities; (2) being relatively simple and inexpensive since it does not require a separate measuring container and a means for distributing the liquid into and out of that measuring container; (3) providing accuracy by counting of the strokes of the pump when the liquid interface reaches a point in the conduit between the pump and the container into which the liquid is to be deposited.

SUMMARY OF THE DRAWINGS

The above noted and other features of the invention will be better understood from the following detailed description when considered with reference to the accompanying drawings, in which:

FIG. 1 is a perspective view of a sample collector in accordance with an embodiment of the invention;

FIG. 3 is a simplified fragmentary perspective view of a portion of the embodiment of FIG. 1;

FIG. 4 is a cross section view of a portion of the embodiment of FIG. 1;

SPECIFIC DESCRIPTION

Figure 2:
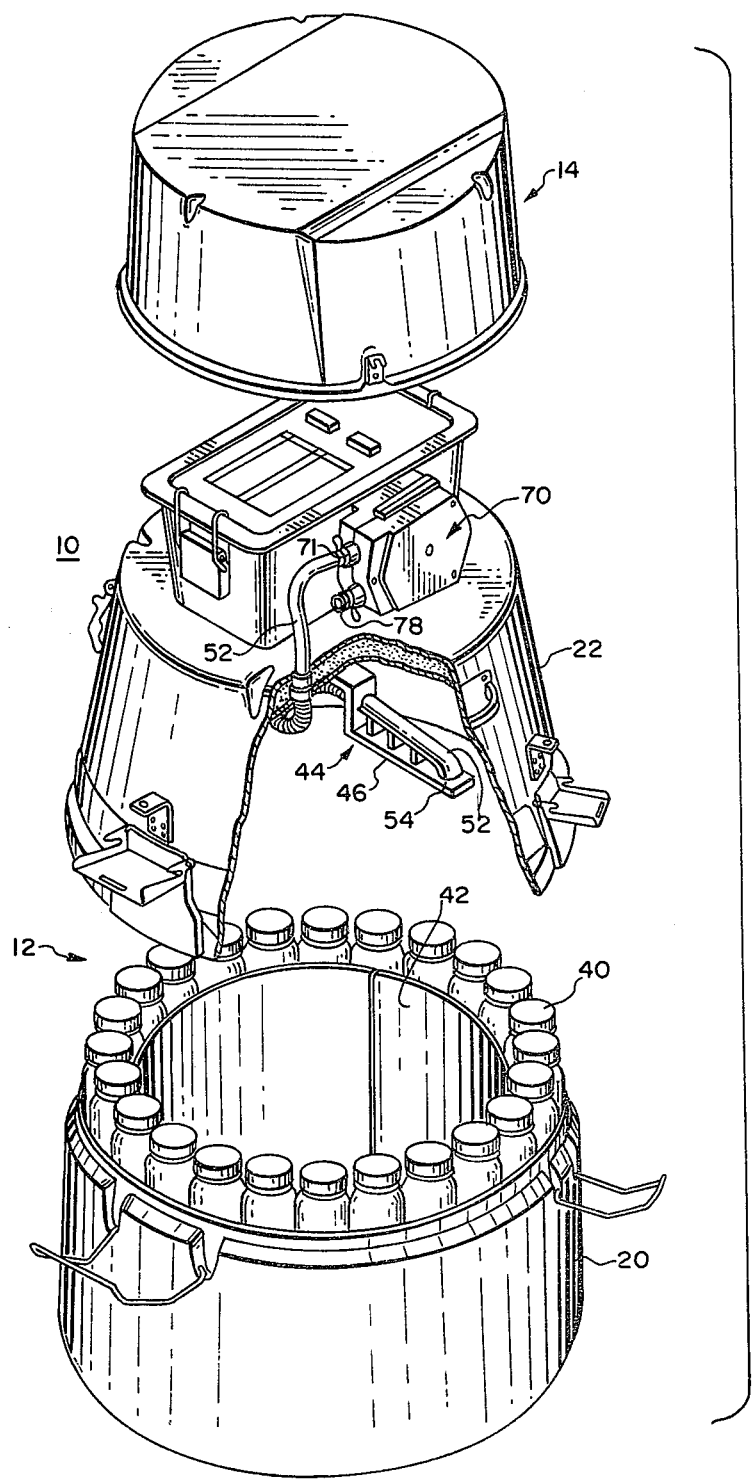
FIG. 2 is an exploded perspective view of the sample collector of FIG. 1, partly broken away to show internal structure.

In FIG. 1, there is shown a liquid sample collector 10, having a generally cylindrical base 12, a cylindrical cover 14 fitted to the base 12 and an intake conduit 16 in the form of a tubular intake hose extending through and depending downwardly from an opening 18 in the upper portion of the base 12.

The base 12 includes a sample bottle tub 20, and a control section 22 positioned to overlie the sample bottle tub 20 and to receive the cover 14. The cover 14 is removably attached to the control section 22 by a plurality of conventional latching mechanisms 26, and the control section 22 is similarly attached to the sample bottle tub 20 by a plurality of latching mechanisms 26.

The sample collector 10 is supported in a suitable position in vicinity of a body of liquid being monitored. The control section 22 includes three cable-harness attaching eyelets 30 (two of which are shown in FIG. 1) to receive the hook of a removable cable harness 32 by which the sample collector 10 may be lowered such as through a manhole or otherwise manipulated and positioned for use.

Prior to operation, the sample collector 10 is programmed to draw liquid at fixed intervals from a body of liquid and deposit the sample drawn after each interval into a different container. Time intervals are set for it to draw a sample or a flow meter may be included in the stream to measure the volume of liquid flowing past a point and initiate the collecting of a sample after that volume of liquid has flowed past the meter. In addition to setting the intervals for taking samples, the volume of the sample taken may be set.

In operation, after the sample collector 10 has been set for predetermined intervals and for the volume of each sample, samples are periodically drawn through the intake conduit 16 and deposited in containers. During the taking of a sample, a liquid interface detector within the sample collector detects the liquid and causes the strokes of the pump to be counted to the predetermined number of counts corresponding to the volume. During this counting, the liquid is deposited in a selected container and then the pump reverses to drive the remainder of the liquid back through the intake conduit 16.

This process is repeated at each selected interval of time or volume of liquid in the main flow stream while the sample collector 10 deposits each sample in a different container.

As best shown in FIG. 2, the bottle tub 20 is generally cylindrical with an open top and closed bottom, thus being adapted to receive a plurality of sample bottles 40 of selected number and arranged in a circle adjacent to the inner cylindrical wall of the bottle tub 20 below the control section 22. A bottle retaining ring 42 retains the sample bottles 40 in their appropriate position within the bottle tub 20.

The control section 22 supports a distributor tube guide assembly 44 above the sample bottles 40, which distributor tube guide assembly 44 acts as a liquid distribution system to apply the collected liquid into a selected one of the plurality of sample bottles 40. The tube guide assembly 44 is formed with a rotating arm 46 mounted for rotation to a centrally-located vertical, rotatable axle (not shown in FIG. 2) for rotation therewith in a horizontal plane above the circle of sample bottles 40.

As schematically shown in FIG. 3, the control section 22 includes the axle 48, a drive motor 50, a control circuit 90, a coded disc and disc reader unit 60 and an interface detector 92. The upper end of the axle 48 is operatively coupled to the drive motor 50 through which the rotating arm 46 is intermittently swung above each of the sample bottles 40 such that a selected discrete liquid sample is discharged into each of the sample bottles 40 in a programmed manner. Because FIG. 3 is schematic, it does not show the actual configuration of the arm 46 and specifically omits the L-shape shown better in FIG. 2 together with certain supports 54 which hold the distribution conduit 52 as the arm 46 rotates and positions the outlet port over the openings of the sample bottles 40.

To position the distribution conduit 52 over the openings in the sample bottles 40, the optically coded disc and disc reader unit 60 is located within the control section 22, with the disc mounted for rotation with the axle 48 so as to assume a rotary position at the same angle as the exit port of the distribution conduit 52. At each angle of rotation corresponding to a different one of the sample bottles 40, the coded disc and disc reader unit 60 detects a signal on the disc and halts the rotation so that the exit port of the distribution conduit 52 is positioned over the sample bottles 40.

To drive the axle 48 and thus the liquid distribution system, the drive motor 50 rotates the axle 48 together with the optical disc in the coded disc and disc reader unit 60. This drive motor 50 may be any conventional type of electric motor and may be battery driven or driven from the main supply.

To draw liquid from a body of liquid and force it through the distribution conduit 52 into the sample bottles 40, a peristaltic pump 70 is mounted in the control section 22 with the distribution conduit 52 communicating with it on the outlet side of the pump and the intake conduit 16 communicating with the intake side. The interface detector 92 is connected to the peristaltic pump 70 through the control circuit 90 to provide partial control of the peristaltic pump 70.

The interface detector 92 is an optical sensor although any of the commercially available or commonly used detectors may be used such as conductivity probes, contact probes, ultrasonic probes, capacitive sensors or the like. It is located below the peristaltic pump 70 near the bottom of the control section 22 so as to provide only a short length of distribution conduit 52 between the interface detector 92 and the sample bottles 40.

To reduce the weight of liquid against which the pump acts, the interface detector 92 is located between the exit port of the peristaltic pump 70 and the exit port of distribution conduit 52 so that the liquid interface at detection has reached a location where the liquid one one side of the pump in the intake conduit 16 has its weight balanced by the weight of the liquid in the distribution conduit 52 on the other side of the pump, thus reducing the load on the pump. The liquid beyond the pump, because it is flowing downwardly, fills the tube and is less subject to having bubbles in it because of the lifting force of the pump working against its weight since its weight and the force of the pump are additive here.

In FIG. 4, there is shown a sectional view of the optical interface detector 92 having a plastic casing 150, the silicone rubber pump tube 52, the light sensor 152 and the source of light 154. The plastic housing is a right regular parallelopiped of opaque material.

The silicone rubber pump tube 52 is sufficiently thin to be translucent and passes through the plastic housing 150 in a first direction orthogonal to an entering surface and an exit surface so that its cylindrical walls are parallel to two parallel continuous side surfaces, to a light-source holding side perpendicular to the continuous side surfaces and to a light sensor side surface perpendicular to the two continuous side surfaces and parallel to the light source holding surface.

To mount the light source 154, the plastic housing 150 has a cylindrical hole smaller in diameter than the diameter of the tube 52 in the light-source holding side which receives the light source 154 and mounts it at a location adjacent to the outer wall of the silicone rubber tube 52 with its conductors extending outwardly. The light source 152 is an infrared light-emitting diode (LED) such as TIL52 manufactured by Texas Instruments.

To mount the light sensor 152 the plastic housing 150 has a cylindrical hole substantially of the same diameter as the hole 154 extending coaxially with it through the light sensor side of the plastic housing. This hole receives the light sensor 152 and mounts it at a location adjacent to the outer wall of the silicone rubber tube 52 with its conductors extending outwardly. This sensor may be any suitable infrared sensor such as an infrared phototransistor of the type manufactured and sold by Texas Instruments under the designation TI L78.

The tube, light source and light sensor are selected to work together so that there is a sufficient difference in the intensity of the infrared light transmitted through the tube 52 from the light source when there is no infrared absorbing liquid in the tube from which it is substantially full of such liquid as to drive the light sensor into a state of conductivity substantially different when the tube is full from that when it is empty.

Figure 5:
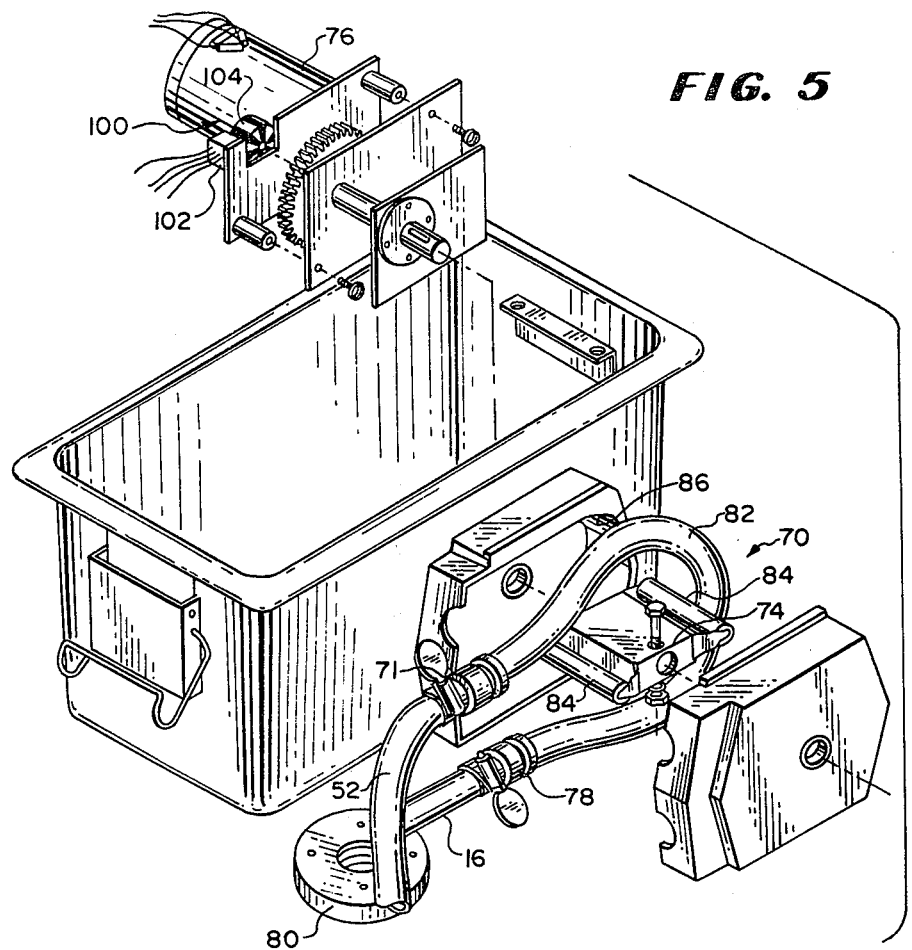
FIG. 5 is a simplified fragmentary view of a portion of the sample collector of FIG. 1.

As best shown in FIG. 5, the peristaltic pump 70 includes a rotor 74, a flexible internal conduit 82, a pump motor 76, and a revolution pulse generator 100. The pump motor 76 drives the rotor 74 through a common shaft and its revolutions are counted by the revolution pulse generator 100.

To provide pumping action, the rotor 74 includes radially positioned rollers 84 on each end which are rotated about the common shaft and into contact with the flexible internal conduit 82 to force fluid therethrough. At one end of the internal conduit 82 is a connector 71 for causing that end of the conduit to communicate with the inside of the distribution conduit 52 for applying fluid to the sample bottles 40 (FIG. 3). At the other end is another connector 78 for connecting the conduit to the intake conduit 16 to receive fluid through an inlet suction cup 80. The intake conduit 16 is shown broken away and normally the inlet suction cup 80 would be some length of tube suitable for depositing in the liquid to be sampled.

The internal conduit 82 is positioned along a curved path with its outer wall of the curve within the radius of the rollers 84 from the central axis of rotation so that as the rotor 74 is turned by the pump motor 76, the rollers 84 alternately compress the conduit and permit it to relax, thus forcing liquid in one direction or the other. The internal conduit 82, the distribution conduit 52 and intake conduit 16 are all of a plastic chemical resistant material to permit flexibility and resist chemical action.

To provide a signal proportional to the pumped liquid, a revolution pulse generator 100 is mounted to the shaft of the pump motor 76 and includes a light sensor 102 and a disc. The disc is mounted to the shaft and rotates with it in front of the light sensor 102 so that the light sensor 102 counts revolutions of the pump motor 76 for control purposes to be described hereinafter.

Figure 6:
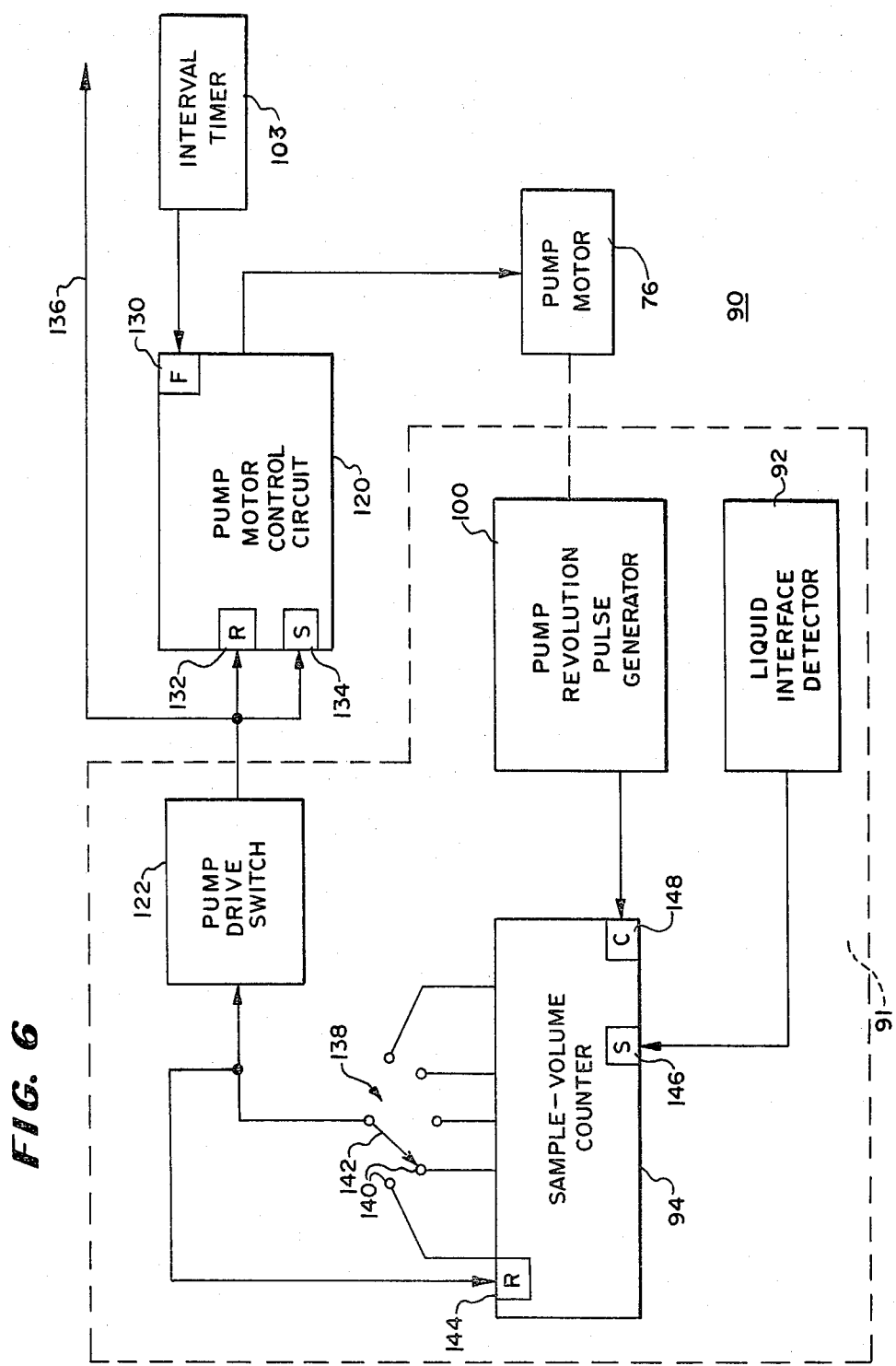
FIG. 6 is a block diagram of a circuit forming a portion of the embodiment of FIG. 1.

As best shown in FIG. 6, the control circuit 90 includes a volume control circuit shown generally at 91, a pump motor control circuit 120 and an interval timer 103. The pump motor 76 is electrically connected to the pump motor control circuit 120 which drives it in the forward or the reverse direction and in turn the pump motor control circuit 120 is connected to and controlled by the interval timer 103 and the volume control circuit 91. The pump motor 76 drives the pump revolution pulse generator 100 shown in FIG. 4. The control circuit 90 serves as a control means that includes a means for controlling the volume of liquid pumped through said conduit.

The volume control circuit 91 is a means for controlling the volume of liquid pumped through said conduit and includes a sample-volume counter 94, a liquid interface detector 92, a pump-drive switch 122, a volume selection switch 138 and the pump revolution pulse generator 100. The pump motor control circuit 120 is controlled by the pump-drive switch 122 to which it is connected. The pump-drive switch 122 is in turn controlled by the sample-volume counter 94 which has its start count input terminal electrically connected to the liquid interface detector 92 and its count terminal electrically connected to the pump revolution pulse generator 100.

To control the pumping of liquid, the pump motor control circuit 120 is electrically connected to the pump motor 76 to drive it in either forward or reverse directions. The interval timer 103 is connected to the forward drive terminal 130 and the pump-drive switch 122 is connected to the stop and reverse terminals 134 and 132 respectively as well as to a conductor 136 which controls the conduit positioning drive motor 50 to position the distribution conduit 52 over successive bottles.

The interval timer 103 and the pump motor control circuit 120 may be substantially the same as described in the aforementioned U.S. Pat. No. 3,838,719 or may be any other type of control circuit and timer to initiate the taking of samples. Instead of the interval timer 103, for example, a flow meter may be connected which will initiate the taking of a sample after a certain volume of fluid has flowed passed the flow meter in a manner known in the art.

In the preferred embodiment a microcomputer performs some of the functions of that circuit together with other functions which are useful in sample collectors generally but not related to the invention. In such an embodiment, the conductor 136 is unnecessary whereas in the embodiment described in U.S. Pat. No. 3,838,719 it is used to start the motor which will move the sample distributing apparatus from location to location.

To control the volume of liquid pumped into a container, the liquid interface detector 92, the pump revolution pulse generator 100, the sample-volume counter 94 and the pump-drive switch 122 cooperated to establish the volume of liquid in each of the sample bottles 40 (FIG. 3). The solid interface detector 92 detects the leading edge of the liquid as described in connection with FIG. 3 at a location close to the exit port 54 of the distribution conduit 52 and applies an enabling signal to the sample-volume counter 94 which is receiving pulses from the pump revolution pulse generator 100. These pulses are generated as the pump motor 76 turn and thus indicate the volume of liquid pumped.

To set the volume of fluid to be inserted in a container, the volume selection switch 138 has a plurality of fixed contacts 140 each connected to different ones of the outputs of the sample-volume counter 94 and has its armature 142 electrically connected to the reset terminal 144 of the sample-volume counter 94 and to the input terminal of the pump-drive switch 122.

With this arrangement, as the sample-volume counter 94 counts, it eventually reaches a selected one of the fixed contacts 140 which causes it to be reset and causes the pump-drive switch 122 to be energized to stop and reverse the pump motor control circuit 120. The sample-volume counter 94 does not again begin counting until its enabling terminal 146 receives a pulse from the liquid interface detector 92. At that time it begins counting pulses applied to terminal 148 by the pump revolution pulse generator 100 as driven by the pump motor 76. Thus, the setting of volume selection switch 138 controls the amount of fluid which is pumped beyond the liquid interface detector 92 within the distribution conduit 52 (FIG. 3).

While a hardware circuit is described in FIG. 5, it is preferable in most applications to use a single microprocessor to control the functions of the invention described herein as well as other functions of the sample collector. In such an embodiment, the liquid interface detector 92 applies a signal through buffer circuitry to the microprocesser which then begins counting pulses from the pump revolution pulse generator 100 in a software counter in a manner known in the art. When the preprogrammed limit for the volume of fluid is reached, the central processer applies a pulse through buffer circuitry to the pump motor control circuit 120 to stop the pump motor 76 and reverse its direction. Obviously, any microprogrammer may be programmed to perform the simple functions and economically may be programmed to perform other functions as desired by the designers of the sample collector.

As can be understood from the above description, the sample collector of this invention has the advantages of being relatively simple in structure and of nonetheless being able to apply a controlled volume of liquid to each of a series of containers accurately.

Although a preferred embodiment of the invention has been described with some particularly, many modifications and variations of that embodiment may be made without deviating from the invention. Therefore, it is to be understood that, within the scope of the claims, the invention may be practiced otherwise than as specifically described.

What is claimed is:

1. A sample collector for transferring liquid from a body of liquid to plurality of containers comprising:
    a conduit means having a flow passage, an inlet port and an outlet port;
    said inlet port being adapted to be inserted in a body of liquid;
    means for positioning said outlet port sequentially over certain of said plurality of containers, whereby samples of said liquid may be inserted into said containers;
    pump means operatively coupled to said conduit means for selectively pumping liquid through said flow passage between said inlet port and said outlet port for insertion into said different ones of said plurality of containers;
    control means coupled to said pump means for controlling the pumping operation thereof;
    detection means operatively coupled to said conduit means at a predetermined position between said pump means and said outlet port for detecting the presence of a liquid interface within said conduit means at said position and providing a signal representative thereof; and
    said control means including means for controlling the volume of liquid pumped through said conduit means by said pump means from the time said interface signal is received, whereby a predetermined volume of liquid is applied to said selected container.

2. A sample collector according to claim 1 in which said control means further includes a means for reversing said pump after said predetermined volume has been pumped into said containers, whereby said fluid passage is cleared.

3. A sample collector according to claim 2 in which said detector means is a means for detecting changes in infrared light absorbance.

4. The sample collector of claim 3 in which:
    said pump means includes a drive means, the motion of which is proportional to the amount of liquid pumped; and
    said control means includes a means for measuring the amount of motion of said drive means and means for applying a signal after a preset amount of motion to said pump means to terminate pumping in the same direction.

5. A sample collector according to claim 4 in which said pump means includes a peristaltic pump and said control means includes counter means for counting revolutions of said peristaltic pump.

6. A sample collector according to claim 1 in which said detector means is a means for detecting changes in capacitance.

7. The sample collector of claim 6 in which:
    said pump means includes a drive means, the motion of which is proportional to the amount of liquid pumped; and
    said control means includes a means for measuring the amount of motion of said drive means and means for applying a signal after a preset amount of motion to said pump means to terminate pumping in the same direction.

8. A sample collector according to claim 7 in which said pump means includes a peristaltic pump and said control means includes counter means for counting revolutions of said peristaltic pump.

9. The sample collector of claim 1 in which:
    said pump means includes a drive means, the motion of which is proportional to the amount of liquid pumped; and
    said control means includes a means for measuring the amount of motion of said drive means and means for applying a signal after a preset amount of motion to said pump means to terminate pumping in the same direction.

10. A sample collector according to claim 9 in which said pump means includes a peristaltic pump and said control means includes counter means for counting revolutions of said peristaltic pump.

* * * * *